(12) United States Patent
Khan et al.

(10) Patent No.: US 9,109,198 B2
(45) Date of Patent: Aug. 18, 2015

(54) AUTOMATED SYSTEMS AND METHODS FOR ISOLATING REGENERATIVE CELLS FROM ADIPOSE TISSUE

(75) Inventors: Zaeem Ashraf Khan, Albany, NY (US); Aaron Joseph Dulgar-Tulloch, Ballston spa, NY (US); Stefan Rakuff, Clifton Park, NY (US); Philip Alexander Shoemaker, Scotia, NY (US); Erik Leeming Kvam, Albany, NY (US); Xiaohui Chen, Niskayuna, NY (US); Jaydeep Roy, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 829 days.

(21) Appl. No.: 13/097,827

(22) Filed: Apr. 29, 2011

(65) Prior Publication Data

US 2012/0276628 A1    Nov. 1, 2012

(51) Int. Cl.
*C12N 5/077* (2010.01)
*C12M 1/40* (2006.01)
(Continued)

(52) U.S. Cl.
CPC .............. *C12M 45/09* (2013.01); *B01F 5/0057* (2013.01); *B01F 5/0206* (2013.01); *B01F 5/0231* (2013.01); *B01F 5/0256* (2013.01); *B01F 5/10* (2013.01); *C12M 27/00* (2013.01); *C12M 47/04* (2013.01); *C12N 5/0653* (2013.01);
(Continued)

(58) Field of Classification Search
USPC .......... 366/165.3–165.5, 165.1, 167.1–167.2, 366/169.1–169.2; 422/536
See application file for complete search history.

(56) References Cited

U.S. PATENT DOCUMENTS 2,459,636 A * 1/1949 Fenney .......................... 568/790
3,870,789 A * 3/1975 Mikat ........................ 435/40.52
(Continued)

FOREIGN PATENT DOCUMENTS

CN    201321454 Y    10/2009
WO    9800247 A1    1/1998
(Continued)

OTHER PUBLICATIONS

Mostafa Barigou et al.,"Bubble-size Distributions in a Mechanically Agitated Gas-Liquid Contactor", Chemical Engineering Science, vol. 47, Issue 8, pp. 2009-2025, Jun. 1992; 3 Pages.
(Continued)

*Primary Examiner* — Jill Warden
*Assistant Examiner* — Julie Tavares
(74) *Attorney, Agent, or Firm* — Jenifer E. Haeckl (57) ABSTRACT

A method of processing an adipose tissue to collect adipose derived regenerative cells is provided, wherein the method comprises providing a vessel comprising a fluid jet mixer; introducing the adipose tissue into the vessel; introducing a buffer solution into the vessel; washing the adipose tissue using the fluid jet mixer; introducing an enzyme solution into the vessel; initiating jet mixing into the vessel comprising the adipose tissue, the enzyme solution, and the buffer solution using the fluid jet mixer to digest the adipose tissue to form a digestion product; phase-separating the digestion product into a digested buoyant fat layer and a non-buoyant aqueous layer; and collecting the non-buoyant aqueous layer comprising the adipose derived regenerative cells. A system of processing an adipose tissue to collect adipose derived regenerative cells is also provided.

11 Claims, 7 Drawing Sheets

(51) Int. Cl.

| | | |
|---|---|---|
| *C12M 1/00* | (2006.01) | |
| *B01F 5/02* | (2006.01) | |
| *C12M 1/02* | (2006.01) | |
| *B01F 5/00* | (2006.01) | |
| *B01F 5/10* | (2006.01) | |

(52) U.S. Cl.
CPC ....... *C12N2501/70* (2013.01); *C12N 2501/734* (2013.01); *C12N 2521/00* (2013.01)

(56) References Cited

U.S. PATENT DOCUMENTS

| | | | |
|---|---|---|---|
| 3,880,409 | A | 4/1975 | Bok et al. |
| 5,721,120 | A | 2/1998 | Seifert et al. |
| 5,824,354 | A | 10/1998 | Ritter et al. |
| 7,901,672 | B2 | 3/2011 | Fraser et al. |
| 2003/0211928 | A1* | 11/2003 | Dolecek et al. ........... 494/37 |
| 2008/0031317 | A1 | 2/2008 | Kurz et al. |
| 2010/0279405 | A1 | 11/2010 | Peterson et al. |
| 2010/0285521 | A1* | 11/2010 | Vossman et al. ........... 435/34 |
| 2010/0285588 | A1* | 11/2010 | Stubbers et al. .......... 435/379 |
| 2012/0100611 | A1 | 4/2012 | Kensy et al. |

FOREIGN PATENT DOCUMENTS

| | | |
|---|---|---|
| WO | 03024215 A1 | 3/2003 |
| WO | 2012047286 A1 | 4/2012 |

OTHER PUBLICATIONS

Search Report and Written Opinion from corresponding PCT Application No. PCT/SE2012/050442 dated Jul. 25, 2012.

European Search Report issued in connection with corresponding EP Application No. 12776983.4-1501 on Nov. 6, 2014.

* cited by examiner

AUTOMATED SYSTEMS AND METHODS FOR ISOLATING REGENERATIVE CELLS FROM ADIPOSE TISSUE

FIELD

The invention relates to systems and methods for isolating regenerative cells, and more particularly to systems and methods for isolating regenerative cells from adipose tissue.

BACKGROUND

Regenerative cells are useful for various therapeutic applications, such as tissue engineering, and regenerative medicine. For example, regenerative medicine aims to regenerate damaged tissue by stimulating the damaged organ or tissue, by healing them and producing regenerative cells. The regenerative cells improve the condition of a diseased state. For example, it is used to regenerate heart muscles to replace damaged heart tissue after heart attack. A tissue comprising regenerative cells can be cultured in the laboratory, and used to facilitate organ or tissue transplantation into a patient as per the patient's need.

Adipose tissue is recognized as an accessible and reliable source for isolation of the regenerative cells. A population of adipose derived regenerative cells comprises several cell types, such as adult stem cells, pre-adipocyte, fibroblast, endothelial progenitor cells, vascular endothelial cells, and vascular smooth muscle cells among others. Various methods have been explored to extract regenerative cells from the waste product after cosmetic surgery, such as abdominoplasty or liposuction procedures. The adipose tissue is digested using lytic enzymes to release heterogenous population of regenerative cells, which contribute to wound repair through a variety of mechanisms by promoting blood vessel growth and blocking apoptosis. Adipose derived regenerative cells can differentiate into several tissue types, such as bone, cartilage, fat, skeletal muscle, smooth muscle and cardiac muscle.

Although various methods and systems for isolating adipose derived regenerative cells are known in the art, the isolation of cells with high quality, and in sufficient quantity for use in the therapeutic application, are unmet needs. Moreover, current methods for isolating adipose derived regenerative cells require different steps including digestion of adipose tissue, various filtration steps, and centrifugation processes, which make the methods more time consuming, expensive, elaborate, and complicated. The current systems, for isolating adipose derived regenerative cells, are more complex because they require several compartments, separate machinery or parts for various functions such as mixing, separation, or centrifugation.

A significant simplification in the design of a system is needed which does not require, for example, propellers, fans, paddles, and a centrifuge or vortex for fluid agitation. Each of these components complicates the difficulties associated with maintaining a sterile system and increases costs, device size, and risk of equipment malfunction.

BRIEF DESCRIPTION

The methods and systems of the invention extract regenerative cells from adipose tissue resulting in a high yield and high quality cells. These methods and systems resolve many of the problems associated with current methods for extracting regenerative cells from adipose tissue.

One example of the method of processing an adipose tissue to collect adipose derived regenerative cells, comprises providing a vessel comprising a fluid jet mixer capable of generating a high velocity fluid stream; introducing the adipose tissue into the vessel; introducing a buffer solution into the vessel; washing the adipose tissue using the fluid jet mixer; introducing an enzyme solution into the vessel; initiating the jet mixer to digest the adipose tissue to form a digestion product; phase-separating the digestion product into a digested buoyant fat layer and a non-buoyant aqueous layer comprising the adipose derived regenerative cells; and collecting the non-buoyant aqueous layer.

In at least one embodiment of the system, the mixing vessel for processing an adipose tissue to collect adipose derived regenerative cells, comprises: at least one inlet port; a centrally located cylinder comprising one or more nozzles configured to generate a high velocity fluid stream; at least one outlet port, wherein the cylinder is operably connected to the inlet port and the outlet port.

At least one embodiment of the system for isolating regenerative cells from an adipose tissue, comprises: a mixing vessel comprising: at least one inlet port; a centrally located cylinder comprising one or more nozzles configured to generate a high velocity fluid stream; at least one outlet port for draining out a fluid, wherein the cylinder is operably linked to the inlet port and the outlet port; one or more containers; and one or more fluid circuit tubing operably connected to the mixing vessel, and to the containers.

DRAWINGS

These and other features, aspects, and advantages of the present invention will become better understood when the following detailed description is read with reference to the accompanying drawings in which like characters represent like parts throughout the drawings, wherein.

These and other features, aspects, and advantages of the present invention will become better understood when the following detailed description is read with reference to the accompanying drawings in which like characters represent like parts throughout the drawings, wherein.

DETAILED DESCRIPTION

One or more examples of methods for processing an adipose tissue to collect adipose derived regenerative cells are provided, wherein the methods comprise various steps including washing and digestion of adipose tissue, and then separating regenerative cells from a fat layer. One or more embodiments of a system for processing adipose tissue to collect adipose derived regenerative cells are also provided.

To more clearly and concisely describe and point out the subject matter of the claimed invention, the following definitions are provided for specific terms, which are used in the following description and the appended claims. Throughout the specification, use of specific terms should be considered as non-limiting examples.

As used herein, the term "adipose derived cells" refers to cells that originate from adipose tissue. The cell population isolated from adipose tissue is a heterogeneous cell population including, but not limited to regenerative cells.

As used herein, the term "jet mixing" refers to a mixing process, wherein the driving force of the mixing process is a hydraulic force. A high velocity fluid stream or fluid jet is produced to generate a jet mixing. In one example, the jet mixer uses a centrifugal hydraulic force generated by using a pump to force fluid-flow through one or more nozzles, creating high velocity streams to mix the fluids in the vessel.

In one example, a method of processing an adipose tissue to collect adipose derived regenerative cells comprises the steps of: providing a vessel comprising a fluid jet mixer capable of generating a high velocity fluid stream; introducing the adipose tissue into the vessel; introducing a buffer solution into the vessel; washing the adipose tissue using the fluid jet mixer; introducing an enzyme solution into the vessel; initiating the jet mixer to digest the adipose tissue to form a digestion product; phase-separating the digestion product into a digested buoyant fat layer and a non-buoyant aqueous layer comprising the adipose derived regenerative cells; and collecting the non-buoyant aqueous layer.

The vessel may be a flexible or a rigid container. For example, the vessel may be a cylinder, a bottle, a flask, a tank, a carrier or a bag. The term "vessel" for mixing adipose tissue, enzymes and buffer solution for processing adipose tissue may be interchangeably used herein with "mixing vessel". The vessel may be made of polymer or glass. The top of the mixing vessel may be sealed via a stopper, lid, or other method, or may be constructed without a sealable opening. The vessel comprises a fluid jet mixer comprising one or more nozzles. The jet mixer is capable of generating a high velocity fluid stream into the vessel. The high velocity fluid stream disrupts the adipose layer and helps mixing various fluids in the vessel. The location, orientation and number of nozzles have significant impact on the quality of mixing of the fluids as well as the product formed.

In one example of a method, the adipose tissue is introduced into the vessel via an inlet port. In a typical operation, adipose tissue is poured into the vessel through a funnel attached to the inlet port. In another example, the adipose tissue may be delivered directly into the vessel via a liposuction cannula. In one example, the adipose tissue is human adipose tissue. The source of human adipose tissue may be, for example, the resulting or waste products after abdominoplasty or liposuction procedures, or may be collected for the isolation of regenerative cells. The adipose tissue may be delivered to the vessel manually or automatically.

In some examples, the buffer solution may be introduced into the vessel via an inlet port. The buffer solution may be introduced into the vessel via the nozzles of the fluid jet mixer. In some examples, the buffer solution is introduced into the vessel before or after addition of adipose tissue, or in gradual or alternating steps. The buffer solution may be delivered to the vessel manually or automatically.

At least one example of the method of mixing fluids uses the fluid jet mixer, referred to herein as "jet mixing", wherein the driving force in the jet mixer is a hydraulic force rather than a mechanical force. In one example, the jet mixer uses a centrifugal hydraulic force generated by using a pump to force fluid-flow through the nozzles within a vessel (or container), creating high velocity streams to mix the fluids in the vessel. In some examples, the jet mixing is initiated when the buffer solution is introduced.

The jet mixing triggers intensive washing of the adipose tissue. The buffer solution is injected and circulated in the vessel. The buffer solution is dispensed through the outlet port and further re-injected into the vessel through the jet mixer, and the washing process is repeated, for example, about 1 to 5 times, and in a given status, may be washed more or less depending on the tissue quality or user need. In a typical example, the process is repeated for 3 to 5 times. The re-injection forces the buffer solution to mix with the adipose tissue due to the kinetic energy of the fluid stream. In one example, the buffer solution is a Ringer's solution. The buffer solution is circulated through the adipose tissue, and the red colored aqueous layer comprising one or more components of blood may be removed from the vessel, for example, by draining it out of the vessel. The washing of the adipose tissue is repeated until the red colored aqueous layer turns light pink and then translucent, which indicates that washing is completed by removing the majority of blood components present in the adipose tissue.

In one example, the enzyme solution is introduced into the vessel via an inlet port. The enzyme solution may be introduced via the same inlet port through which the adipose tissue is introduced, or a different inlet port. The enzyme solution, in one example, is added manually using a syringe or any other injecting device. In another example, the enzyme solution is stored in a container, which may be operably connected to the vessel and the enzyme may be added automatically to the mixing vessel. The enzyme solution is generally introduced after washing the adipose tissue. The concentration of the enzyme, temperature of the digestion process, and digestion time may influence the digestion procedure to the extent at which the viable cells are dispersed from the tissue. The steps of washing and digestion of the adipose tissue is performed in a range from about 20° C. to 40° C. In one example, the steps of washing and digestion of the adipose tissue is performed at 37° C.

In one example of a method, the digestion of the adipose tissue employs bathing of the tissue in an enzyme cocktail using gentle agitation to extract intact cells from the extracellular matrix of adipose tissue. The enzyme cocktails generally comprise collagenase to specifically digest collagens of the extracellular matrix. The enzyme cocktail may also comprise proteases, such as dispase or thermolysin to cleave non-collagen matrix proteins. The enzyme-cocktail may also include neutral proteases, lipase, hyaluronidase, deoxyribonuclease, or trypsin. The enzymes may be free of viable micro-organisms and other contaminants, such as endotoxin. In one embodiment, the enzymes may be GMP (good manufacturing practice) grade for human therapeutic application. In one example, the enzyme used for digestion of the adipose tissue is collagenase.

At least one example of the method employs the jet mixing that provides a gentle agitation for digesting adipose tissue to extract viable cells. In some examples, the jet mixing is initiated by starting the jet mixer followed by addition of enzyme solution. In some other examples, the jet mixing is initiated by introducing the buffer solution to wash the adipose tissue using the fluid jet mixer. The jet mixing triggers intensive mixing of the enzyme solution and the adipose tissue which causes extensive digestion of the adipose tissue. During jet mixing, only the mixing loop (a line for buffer supply to the mixing vessel) and the outlet port of the vessel are open, which forms a closed loop for repeated fluid mixing into the vessel. The cycle of fluid mixing and digestion repeats to increase the yield of the digestion product. The jet mixing cycle for digestion of adipose tissue lasts, for example, for about 10 to 60 minutes, or it may vary depending upon the concentration of the enzyme, pump speed, volume flow rate through the fluid circuit, orientation and number of nozzles, shape of the mixing vessel, tissue quality or user need. In one typical example, the digestion time may be in a range of 10 to 15 minutes or more depending on various conditions of the digestion, such as enzyme concentration, temperature of the digestion medium, or extent of fluid mixing. The jet mixing allows a shorter digestion cycle. In jet mixing, the enhanced mixing reduces the digestion time, as well as the overall cycle time for processing adipose tissue.

In one example of method, the fluid is drawn out of the vessel via the outlet port comprising a filter unit and the filtered fluid is re-injected into the vessel through the jet mixer for further digestion of the undigested tissue. The filtered fluid comprising extracted cells, enzymes and buffer solution, is re-injected and run the mixing cycle for further digestion of the tissue depending on enzyme concentration, tissue quality or user need to secure complete digestion of the adipose tissue for obtaining maximum yield of the regenerative cells. In one embodiment, the digestion time is a combination of washing time and digestion time, while the cycles run simultaneously.

In one or more embodiments, the system is devoid of filter unit. For example, the outlet port lacks any filter. In one embodiment, the buoyancy of adipose tissue is balancing with the mixing speed of the fluid to prevent tissue intake into the pumps. In the embodiments, where there is no filter in the mixing vessel, allows tissue pieces to circulate through the fluid circuit, although most of the tissue remains in the mixing vessel due to buoyancy.

In some examples of the method, the digestion of adipose tissue results in a buoyant layer comprising fat and mature adipocytes, and a non-buoyant aqueous layer comprising regenerative cells. Following digestion, the contents of the vessel are allowed to settle, for example, about 5 to 10 minutes or it may vary depending on the tissue quality or user need until the formation of a clear phase separation of the digested buoyant fat layer and the non-buoyant aqueous layer. The wait time for phase separation is dependent on the configuration of the system.

In one example of a method, the non-buoyant aqueous layer comprising the adipose derived regenerative cells is collected as a final product. In one example, the non-buoyant aqueous layer is gravity drained into a container for collecting the regenerative cells. The term "container for collecting regenerative cells" is interchangeably used herein with "product-container", or "product-bag". In another example, the non-buoyant aqueous layer comprising the regenerative cells is drained out using a pump or vacuum and collected into the product-container. A connecting tube is present between the mixing vessel and the product-container, and the non-buoyant aqueous layer is collected through the same connecting tube. In one example, the tube that collects the non-buoyant aqueous layer and dispense into the product-container comprises a filter unit, which is embedded into the end portion of the tube present in the product-container. The filter unit prevents tiny tissue pieces from entering into the product-container. In some embodiments, the filter unit has a pore-diameter in a range from about 100 to 300 micron. In one embodiment, the filter unit has a pore-diameter of about 270-micron. In one example, the tube may comprise more than one filter units depending on the requirement of purification extent of the regenerative cells.

In one or more embodiments of a system, a vessel for processing an adipose tissue to collect regenerative cells comprises at least one inlet port comprising one or more nozzles configured to generate a high velocity fluid stream; and at least one outlet port. In one embodiment, the nozzles and the inlet port are configured to generate a tangential flow into the fluid (such as, buffer solution) present in the vessel during operation. In this embodiment, the nozzles and the inlet port are configured in the vessel in such a way, so that during operation the fluid injected through the nozzles and the adipose tissue and/or enzyme solution is injected through the inlet port generating a tangential flow in the fluid stream of the vessel.

In at least some embodiments, the vessel comprises at least one inlet port; a centrally located cylinder comprising one or more nozzles; and at least one outlet port, wherein the cylinder is operably linked to the inlet port and the outlet port. In one example, the nozzles are configured to be in multi direction to generate fluid flow in different directions, such as upward direction, downward direction, tangential direction, outward, inward direction or a combination of one or more of those in the vessel. In one example, the nozzles are configured to be in an upward direction. In this example, the nozzles of the centrally located cylinder configured to generate the fluid stream in an upward direction. The nozzles are configured to be in an upward direction to generate an upward fluid stream and form a jet mixing into the vessel. The cylinder is operably linked to the inlet port, mixing loop, and the outlet port. The vessel further comprises a filter unit connected to the outlet port. In some embodiments, the outlet port is operably linked to a peristaltic pump to drain out the non-buoyant aqueous layer.

Figure 1:
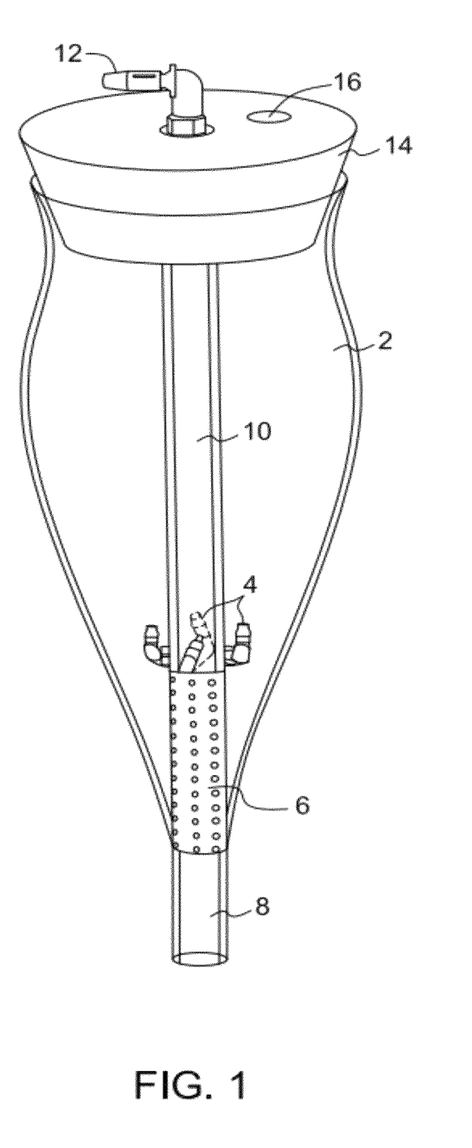
FIG. 1 is a perspective view of an embodiment of a vessel of the invention for processing adipose tissue.

Referring now to FIG. 1, embodiments of a vessel and various parts of the vessel for processing adipose tissue are illustrated. The mixing vessel 2 may be a flexible or rigid container made from polymer, or glass. The vessel may be sealed via a stopper 14. The stopper may be a rubber stopper. The design of the mixing vessel may comprise optional geometric features to enhance mixing or draining. For example, the mixing vessel may comprise the features for better turbulence or agitation of the fluid while mixing. The design of the vessel of FIG. 1 is for processing adipose tissue in a non-sterile condition. The design of the vessel may be modified for processing adipose tissue in a sterile condition. The vessel 2 comprises two inlet ports 12, and 16. The vessel 2 comprises a centrally located cylinder 10. The centrally located cylinder 10 further comprises nozzles 4. A filter unit 6 is attached to the outlet port 8. The filter unit is a cylindrical filter having a pore diameter of about 1.6 mm.

In one embodiment, the centrally located cylinder 10 comprises four nozzles 4. The number of nozzles may be varied depending on the requirement of the process. The nozzles 4 are used for injecting fluids, such as buffer solution, into the vessel. In some embodiments, the nozzles are used for re-injection of the buffer solution, or the fluid comprising enzyme and the buffer solution. In some embodiments, the nozzles are oriented at an angle of 90° bend, in some other embodiments the nozzles are oriented at an angle of 60-70° bend from the vertical plane, or with respect to the central column in the mixing vessel. This configuration of the nozzles creates a turbulent vortex which essentially increase the mixing efficiency due to the fact that, the kinetic energy is dissipated within the fluid as the nozzles are submerged in the fluid.

In one example, a human adipose tissue is poured into the mixing vessel 2 through a funnel attached to the inlet port 16. In one example of the method, the human adipose tissue may be delivered directly into the vessel 2 via liposuction cannula. In one example, the fluid jet comes out of the nozzles 4 creating a turbulent vortex, which results in a well-mixed solution of the adipose tissue, enzyme solution and buffer. The location, orientation and number of nozzles 4 have significant impact on the quality of fluid mixing and the enzymatic digestion during processing of the tissue. The thorough mixing secures extensive enzymatic digestion of the tissue to extract regenerative cells. The filter 6 is embedded into the outlet port 8 in such a way, so that the non-buoyant aqueous layer must pass through the filter 6 before exiting the vessel 2.

Figure 2A:
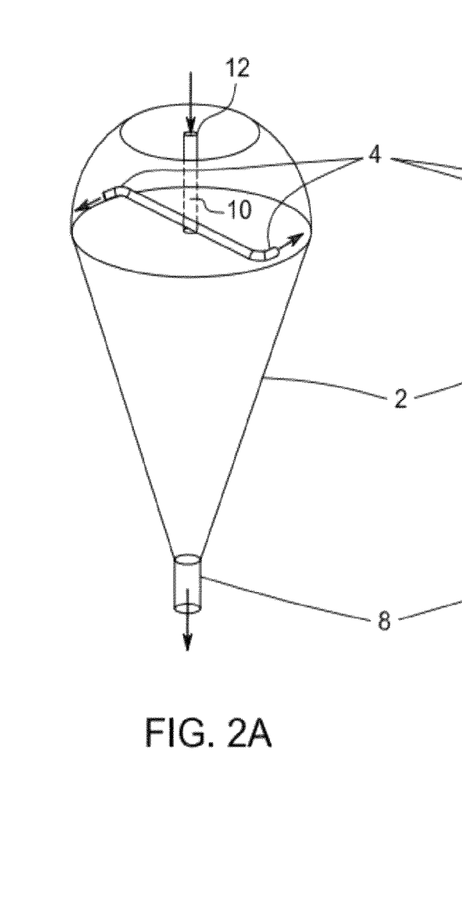
FIGS. 2A-C are schematic drawings of embodiments of the vessels of the invention for processing adipose tissue with varying positions and orientations of nozzles and inlet ports.
Figures 2B, 2C:
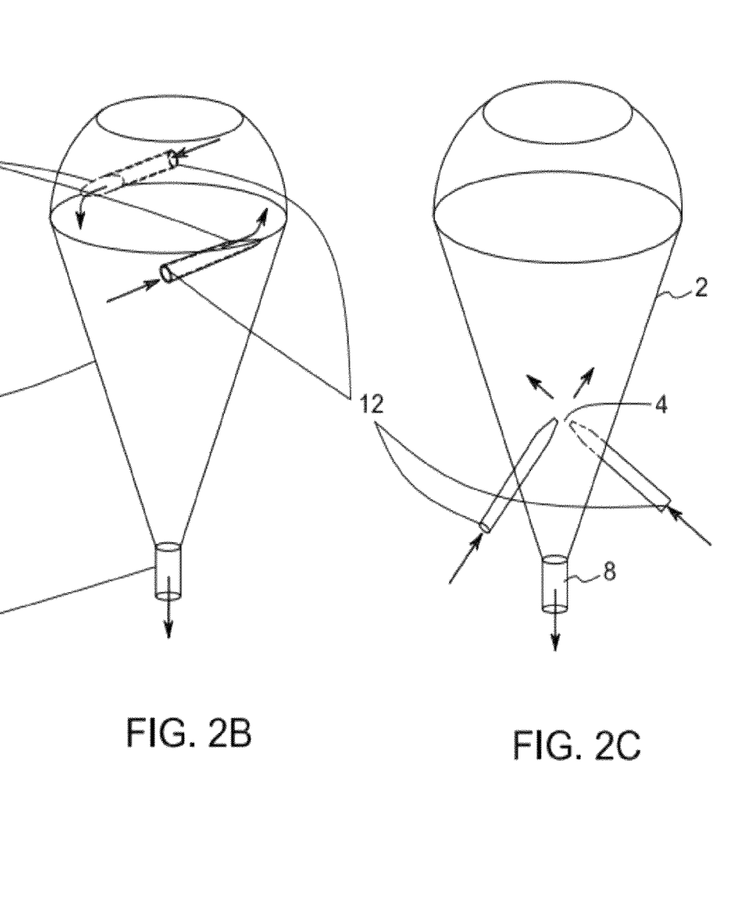

FIGS. 2A, 2B, and 2C illustrate schematic representation of three different designs of the vessel 2 having different orientations of the nozzles 4. FIG. 2A illustrates fluid injection via the centrally located cylinder 10. In this embodiment, nozzles 4 may be oriented in such a way, so that the injection takes place within the fluid comprising the adipose tissue, enzyme solution and buffer solution. In one example, the injection may take place from above the surface of the fluid during processing of the adipose tissue. The embodiment of FIG. 2B illustrates the positions of the nozzles 4 and inlets 12, wherein the nozzles 4 and inlets 12 are embedded in the vessel in such a way, so that the fluid injection occurs tangentially on the surface of the fluid in the mixing vessel 2. In this configuration, the entire assembly may be a single injection molded piece eliminating the central column 10. The embodiment of FIG. 2C illustrates the positions of the nozzles 4 and inlets 12, wherein both of the nozzles and the inlet are part of the mixing vessel 2 and the buffer or enzyme solution is injected into the fluid. Fluid injection as illustrated in this embodiment results in a better mixing compared to injection from above the fluid surface (as shown in FIGS. 2A and 2B). However, any combination of nozzle 4 may be used, and the combination may not be necessarily limited the embodiments depicted in FIGS. 2A-C.

One or more embodiments of a system for isolating regenerative cells from an adipose tissue, comprises a vessel comprising at least one inlet port, a centrally located cylinder comprising one or more nozzles configured to generate a high velocity fluid stream in an upward direction, and at least one outlet port, wherein the centrally located cylinder is operably linked to the inlet port and the outlet port, one or more containers, and one or more fluid circuit tubing operably connected to the vessel, and to the containers. The high velocity fluid stream in an upward direction generates a jet mixing into the vessel.

The term "fluid circuit tubing", interchangeably used herein with "tubes" or "connecting lines", may be made of rigid or flexible material. In some examples, the tubes are in the form of flexible connecting lines made of polyethylene, silicone or any other material. The tubes may vary in size, depending on the requirement of flow rate of the fluid, or the requirement of the amount of fluid to be cycled through the system. The tubes may have varying diameter, length or width. For example, the tube may have a diameter in a range from about 0.05 to about 0.9 inches. In some examples, the diameter of the tube may be increased, if the tissue fraction is also passes through the tube. The volume of fluid, tissue, and buffer solution is controlled to be accurate while transferring from one container to another. The tubes may be capable of withstanding positive pressure, or negative pressure generated in the system.

All the containers or vessels of the system may be comprised of one or more ports, e.g., outlet or inlet ports, which connect with standard syringe and/or suction tubes. The ports may be a sealed port, or may be coupled to cannulas, connecting lines or tubes. In some embodiments of the system, the tubes are coupled to a suction device, such as a syringe or an electric pump operated manually or automatically.

The system further comprises one or more multi-port valves. The tubes may comprise one or more valves, wherein the valves control the fluid-flow through the system. The valves may be selected from hydraulic valves, pneumatic valves, check valves, pinch valves, or mechanical valves. In some examples, there may be a control system to regulate the valves at appropriate time as per requirement of the system. In some examples, the valves may be activated manually. In some other examples, the valves may be activated automatically. In one example, some of the valves may be activated manually and some other valves may be activated automatically.

In one example, the valves may function in combination with one or more pumps. The fluid circuit tubing is operably linked to one or more pumps. The pumps may be selected from peristaltic pumps (positive displacement pumps), reciprocating pumps, hydraulic pumps, centrifugal pumps or combinations thereof. The system further comprises a direct current (DC) servo motor 33, as shown in FIG. 3.

The system may comprise one or more filters. In one embodiment, the filters may be present in one or more containers, tubing or vessel in the system. In one embodiment, the filters may be present in the fluid circuit tubing. Different containers may comprise filters with different pore size. In one embodiment, one or more filters effectively separate the regenerative cells from the tissue chunk. In one embodiment, one or more filters effectively separate regenerative cells from aggregated cell clusters or undesirable cells. The filter used in the system may be general pass-through filters. The filters may be used to remove collagen, adipocyte, lipid, and residual amount of proteolytic enzymes, such as collagenase. In some embodiments, the filters may be used to remove fragmented tissue, or aggregated cells extracted from the adipose tissue or in one embodiment, the filter may be used to concentrate the population of regenerative cells. The filters used herein may be made from polyethersulfone, polyester, PTFE, polypropylene, PVDF, or cellulose. The pore size and shape of the filter, surface area of the filter, flow direction of the solution, trans-membrane pressure, dilution of the cell population, and cell size determine the filtration efficiency as well as viability of the recovered cells. The filters used in outlet port of the mixing vessel may have pore diameter in a range from about 1 to 500 micron. In other embodiments, the filters may be detachable and/or disposable.

Figure 3:
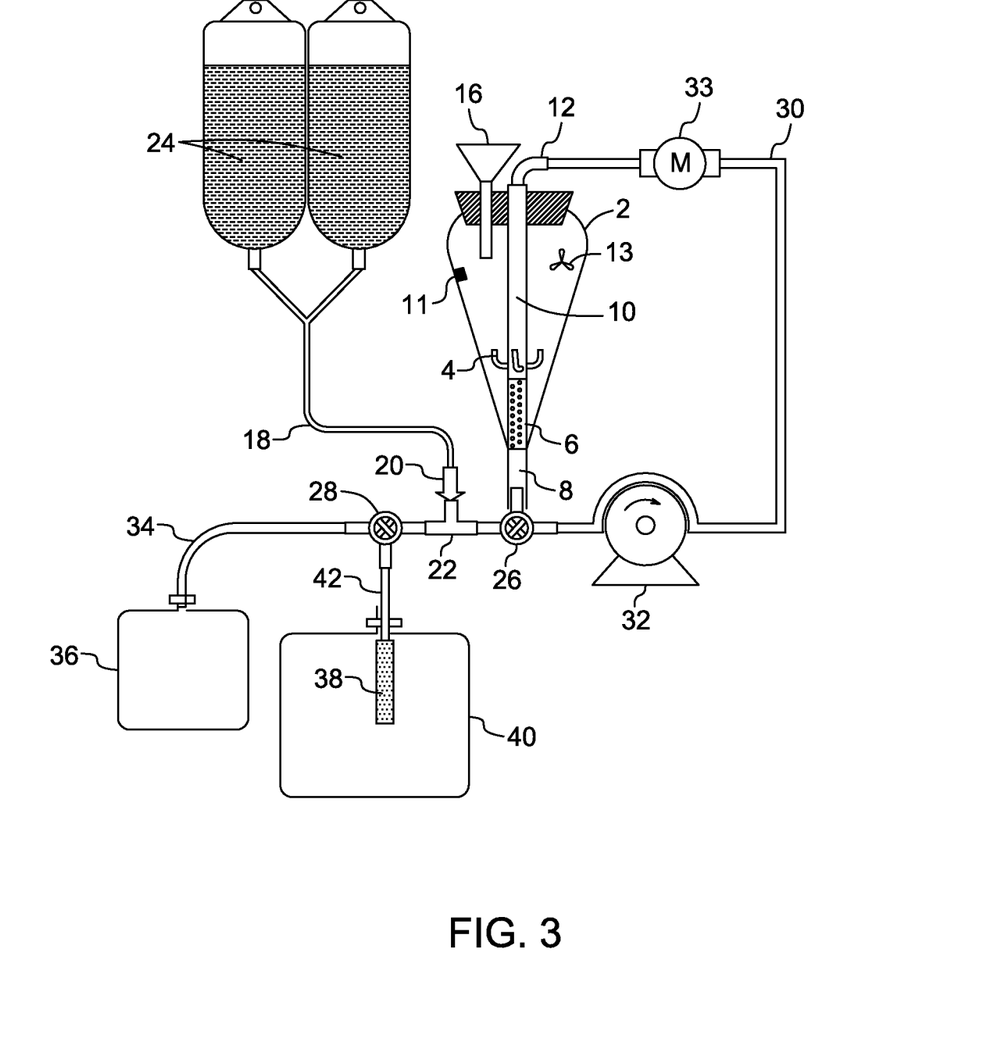
FIG. 3 is a schematic drawing of an example of a system of the invention for processing adipose tissue to isolate adipose derived regenerative cells.
Figure 4:
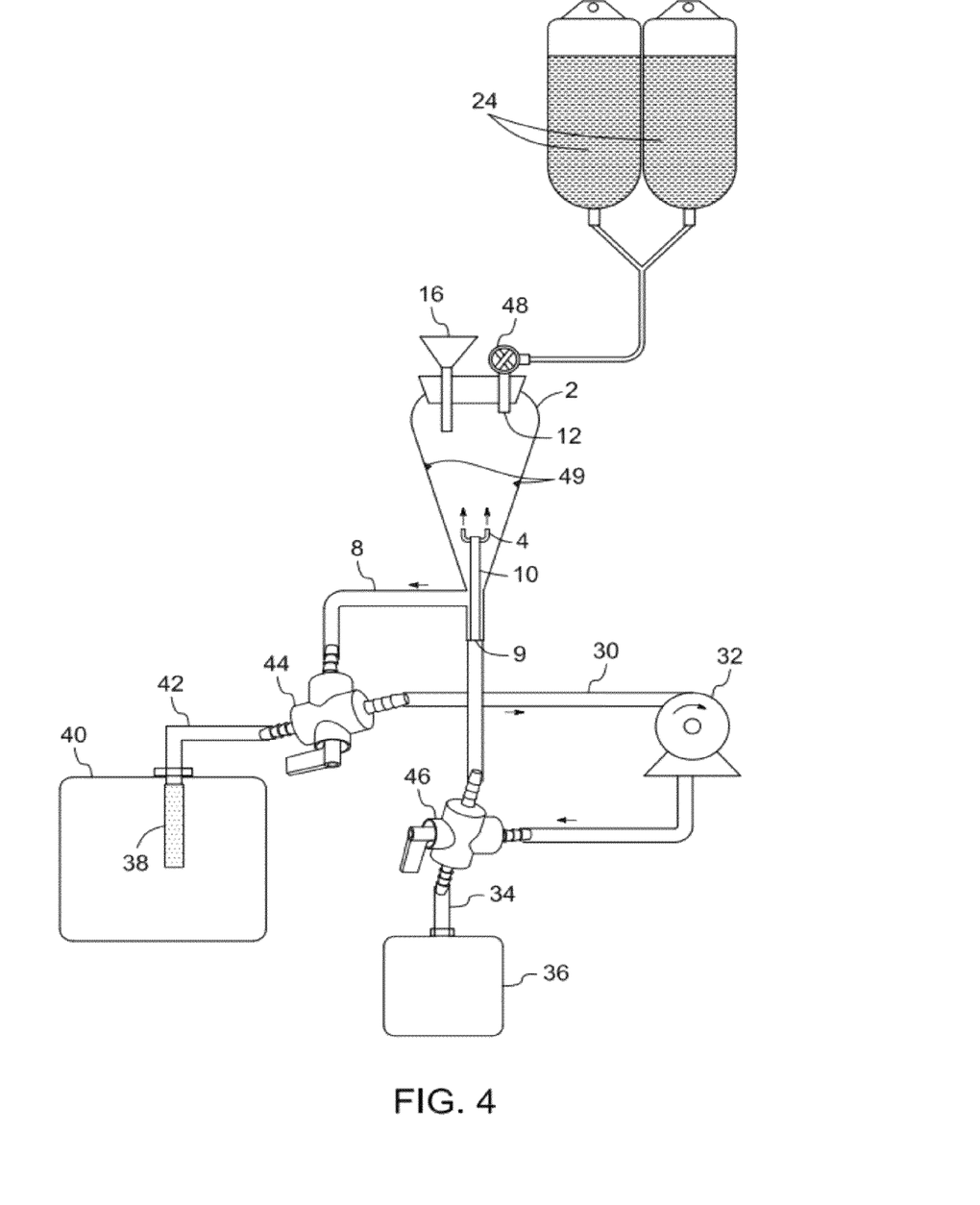
FIG. 4 is a schematic drawing of an example of a system of the invention for processing adipose tissue to isolate adipose derived regenerative cells, wherein a mixing vessel of the system is devoid of a filter unit.

FIGS. 3 and 4 illustrate a schematic presentation of alternate embodiments of system for processing adipose tissue to isolate adipose derived regenerative cells. The system of FIG. 3 employs a mixing vessel 2 comprising four nozzles 4, for injection or re-injection of the fluid into the vessel. One or more optional geometric surface features, such as 49 into the mixing vessel are introduced to enhance mixing. For example, surface features 49 may be turbulators. Apart from the mixing vessel 2, there are three other containers in this embodiment of the system. The Ringer's bags 24 (bags containing Ringer's solution) are configured to hold buffer solution during operation. In one embodiment, the Ringer's bags 24 contain lactated Ringer's solution. The Ringer's bags 24 are connected to the fluid circuit via a T-joint 22. The waste bag 36 is configured to hold waste product of the process, wherein the waste product is drained out via the waste line (or tube) 34. Similarly, line 42 connects the product bag 40 that stores the aqueous solution comprising regenerative cells following the digestion process. A filter 38 is attached to the end of line 42, wherein in one embodiment, the filter unit has a pore diameter of about 270-micron. The filter is used to prevent minute tissue chunks from flowing into the population of regenerative cells.

In one embodiment of the system during operation (as shown in FIG. 3), the fluid flow through the system of FIG. 3 is controlled by using two valves 26 and 28. The peristaltic pump 32 provides a pressure differential to cause the fluid to flow through line 30, which may interchangeably be used herein as the "mixing line". The mixing line 30 is connected to the inlet port 12 of the mixing vessel 2, wherein the inlet port 12 is further connected to the centrally located cylinder or column 10. In this embodiment, the centrally located column is a hollow cylinder and is a part of the mixing loop 30. The centrally located column 10 comprises the nozzles 4. In one embodiment, the system is a 4-jet fluid circuit, which comprises four nozzles for jet mixing into the vessel. Therefore, during operation, the fluid passes through the pump 32, mixing line 30, inlet port 12, and centrally located column 10 and finally exits through the nozzles 4 generating a fluid jet in the vessel. The intersection of the centrally located cylinder 10 and the filter unit 6 is blocked to prevent the fluid from passing through the outlet port without being filtered.

In one embodiment, during the process of washing, valve 28 shuts the waste line 34 and product line 42 and valve 26 shuts the mixing vessel outlet 8. The valve 26 simultaneously opens the mixing line 30. Ringer's solution, which is equal to mass of the tissue, is drawn into the mixing vessel 2 by pump 32 through a check valve 20. The check valve can typically withstand 0.433 psi cracking pressure. The Ringer's solution passes through the mixing line 30, the centrally located column 10 and enters the mixing vessel 2 through the nozzles 4. This injection process causes mixing of the tissue with the Ringer's solution and/or enzyme. The contents of the mixing vessel 2 are allowed to settle until the buoyant tissue pieces settle above the non-buoyant aqueous solution. After a wait period of about 5 minutes, the non-buoyant aqueous layer is gravity drained into the waste bag 36 via valves 26 and 28 through the waste line 34. The process is repeated for about at least 2-times until the red colored aqueous layer turns light pink and translucent, which indicates that washing step is complete.

In the step of digestion, valve 26 shuts the Ringer's line and opens the mixing loop 30 and mixing vessel outlet 8. The fluid is drawn out of the mixing vessel via filter 6 and re-injected through the nozzles 4. Following digestion, the non-buoyant layer is gravity drained into the product container 40. During this process valve 26 shuts the mixing loop 30 and valve 28 shuts the waste line 34. The filter 38 at the end of product line 42 prevents tiny tissue pieces from entering the final product.

The system of FIG. 4 employs a mixing vessel 2 comprising multiple nozzles 4, for injection or re-injection of fluid into the vessel. In one embodiment, the Ringer's bags 24 contain lactated Ringer's solution, and bags 24 are connected to the inlet port through the fluid circuit. The fluid circuit connected to the inlet port via a valve 48. The mixing vessel 2 comprises a column 10. In this embodiment, the column 10 is a hollow cylinder comprises the nozzles 4. In one embodiment, the system is a 2-jet fluid circuit, which comprises two nozzles for jet mixing into the vessel. Therefore, during operation, the fluid enters into the vessel from inlet port through valve 48, comes out of one outlet port 8 and passes through the diverted ball valve 44, enters to the vessel again through the mixing line 30, then through the port 9 at the bottom of the vessel, then through the column 10 and finally enters through the nozzles 4 generating a fluid jet in the vessel.

In FIG. 4, the waste bag 36 is configured to hold waste product of the process, wherein the waste product is coming out from the port 9, passes through the pump 32, and the drained out via a diverted ball valve 46 and through the waste line (or tube) 34.

Therefore, the port 9 functions as an inlet port as well as an outlet port during the processing of adipose tissue to derive cells. Similarly, line 42 connects the product bag 40 that stores the aqueous solution comprising regenerative cells following the digestion process. A filter 38 is attached to the end of line 42, wherein in one embodiment, the filter unit has a pore diameter of about 270-micron. The filter is used to prevent minute tissue chunks from flowing into the population of regenerative cells. The peristaltic pump 32 provides a pressure differential to cause the fluid to flow through line 30, which may interchangeably be used herein as the "mixing line".

In one embodiment of a system of FIG. 4, during the process of washing, valve 46 shuts the waste line 34 and the valve 44 shuts the product line 42, while the fluid circulates through the mixing vessel. After washing of the adipose tissue, the non-buoyant aqueous layer is gravity drained into the waste bag 36 via valves 46 and through the waste line 34. The process is repeated for about at least 2-times until the red colored aqueous layer turns light pink and translucent, which indicates that washing step is complete. After digestion of the tissue pieces, valve 44 shuts the mixing line 30 and opens the product line 42. The fluid is drawn out of the mixing vessel via outlet port 10 and port 9, and the non-buoyant layer is collected to the product container 40. The filter 38 at the end of product line 42 prevents tiny tissue pieces from entering the final product.

Figure 5:
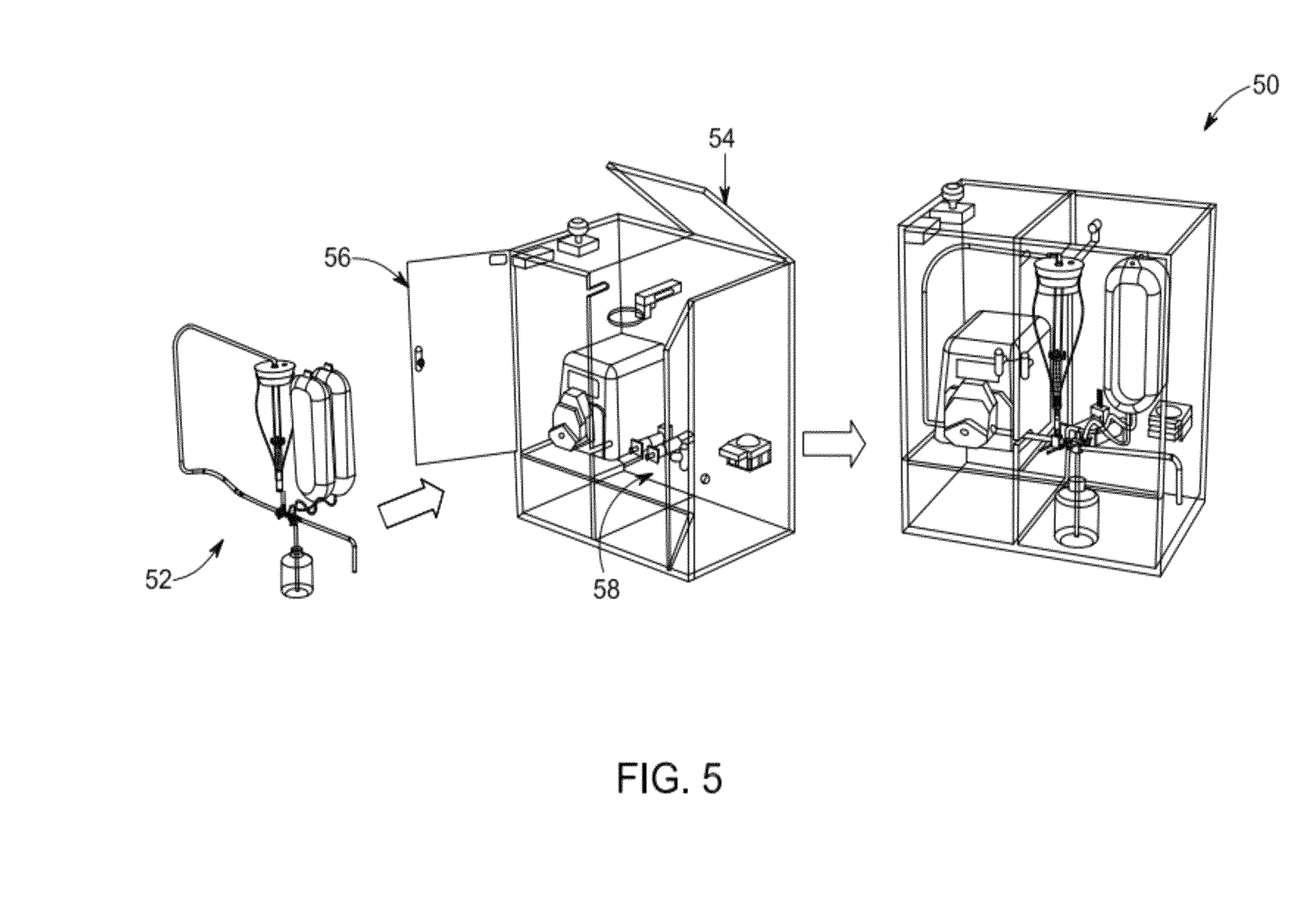
FIG. 5 is a schematic drawing of an example of a method of assembling a system of the invention housed in a chamber.

FIG. 5 illustrates a process of assembling system, wherein the system is housed in a chamber 50. The closed chamber 50 refers to a system, wherein vessels, bags, tubing, and other components may be incorporated in an aseptic or sterile condition. The top of the mixing vessel is sealed with a rubber stopper, wherein typically, the sealed rubber stopper is cleaned by wiping with alcohol, iodine or similar agent. The enclosed system 50 may be opened temporarily maintaining the aseptic condition by using a sterile connecting tubes and parts of the device. The system further comprises one or more clamps (not shown) to control the fluid-flow through the various components of the system. The clamps are useful for maintaining the sterility by effectively sealing different regions of the system. In some embodiments, the process may be operated in a non-sterile condition.

The system housed in a chamber 50 further comprises one or more sensors. The sensors may be selected from optical sensors, ultrasonic sensors, pressure sensors or temperature sensors. The sensors may be capable of distinguishing various features of the system during operation, such as pressure of the fluid, temperature of the inner part of the system, fluid levels, flow rate of the fluid, weight of the containers and weight of the processing vessel. The weight sensor is configured to measure mass of the mixing vessel and mass of the containers.

In some embodiments of the system, the chamber comprises a temperature controller 11, as shown in FIG. 3. The temperature controller may adjust the temperature of the materials present in one or more of the containers or materials passing through the fluid circuit tubing, wherein the materials include tissue, cells, enzymes or buffer solution. The temperature controller 11 may be a heater, or a cooler. In some embodiments, the temperature controller may be switched between a heater and a cooler to maintain desired temperature of the system. For example, the temperature controller may be useful as enzymatic digestion of adipose tissue facilitates in higher temperature, such as at 37° C., whereas the viability of the regenerative cells are higher in lower temperature, such as at about 4° C. In one embodiment, the chamber may comprise a fan heater 13, as shown in FIG. 3.

The system illustrated in FIG. 5 comprises two parts, (1) a fluid circuit, and (2) an automated device. In some embodiments, the fluid circuit is a disposable kit for the device. The automated device automates the washing and the digestion of the adipose tissue. The fluid circuit installed in the device and the device comprises necessary software and hardware to control the valves to regulate the flow, pumps to control the pressure, and sensors for sensing the temperature or pressure in the system and helps controller to control the ideal temperature or pressure for the biochemical processes. The integration of the fluid circuit with the automated device represents the complete device 50 for regenerative cell harvesters from adipose tissue. In this embodiment, the device comprising a chamber comprises three doors: left 56 and right 58 doors in front side, and a top door 54. In this prototype of FIG. 5, a single detachable panel replaces the left and right doors while the depth of the top door is reduced in order to maintain structural stiffness of the enclosure. The detachable front door may be magnetically held in place. The disposable fluid circuit is loaded and unloaded through the front door. The top door is mainly used for pouring tissue sample into the mixing vessel. The entire bottom of the enclosure is sealed on all four sides to contain the fluid in case of rupture of the fluid circuit. The left compartment contains the peristaltic pump, temperature controller, E-stop switch, on-off switch, temperature alarm indicator and power indicator. The right compartment contains the bulk of the fluid circuit, the fan-heater, load sensor, and servo actuators. In one example, during the operation of the device, the right compartment maintains 37° C. using the fan heater. The load sensor and servo actuators are mounted away from the direct blast of the fan heater. Therefore, heat does not affect their operation. The mid wall that separates the right and left compartments has slots cut out in it to accept the tubing. The waste tubing comes out from the right side of the enclosure. The regenerative cells derived from adipose tissue are collected in a sealed container using tubes attached to the vessel outlet port.

The population of regenerative cells collected after processing of the adipose tissue is substantially free from lipid, various components of blood, connective tissue and any other fragmented tissue components. The system generates a heterogeneous population of adipose derived regenerative cells which may be used for research and/or therapeutic applications. In some embodiments, the adipose derived cells are endothelial progenitor cells. In some other embodiments, the adipose derived cells are stem cells. In one embodiment, the cells are safe to use in any therapeutic applications, such as, the cells are suitable for replacement in a tissue and implantation of that tissue in the body of a recipient. In other embodiments, the cells may be used for research purposes, such as, the cells may be used to generate stem or progenitor cell lines.

EXAMPLES

Materials: Lactated Ringer's solution was purchased from Baxter Healthcare Corporation, IL, US and used without further purification. High purity Liberase collagenase and Thermolysin were purchased from Roche, Basel, Switzerland. Cell strainers (100 micron, 40 micron) were purchased from BD Falcon™, NJ, US. Total nucleated cells and dead cells were counted in Nucleocounter, and Nucleocounter was purchased from New Brunswick Scientific (NBS) Company, NJ, US. Normal mouse serum was purchased from Jackson Immuno Research Laboratories, MD, US. Antibodies for flow cytometry were purchased from BD Pharmingen™, CA, US. 1-step Fix/Lyse solution was purchased from eBioscience, CA, US. Multicolor flow cytometry was performed using a Cytomics™ FC-500 flow cytometer, and MXP Software, which were purchased from Beckman Coulter, CA, US.

Example 1

Comparison of Cell Yield Using Jet Mixing and Process Benchmark

Figure 6:
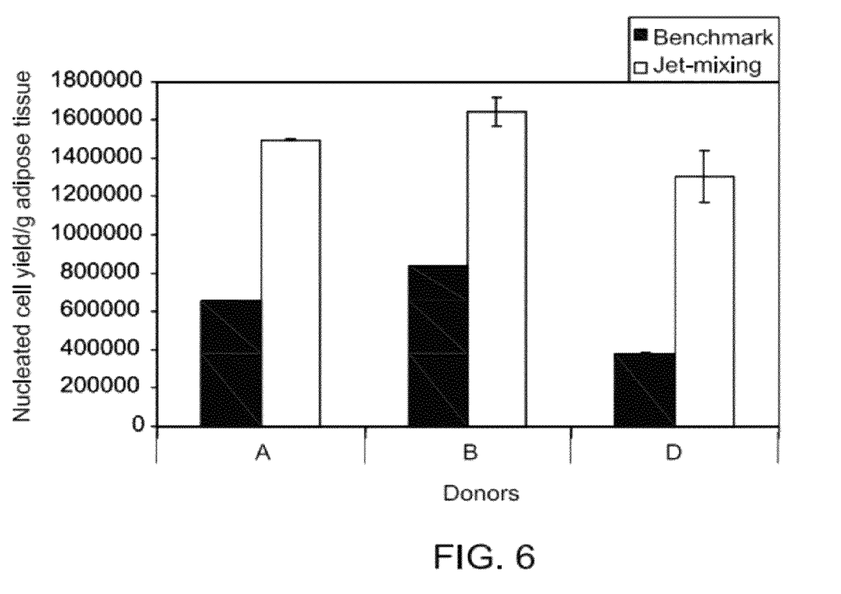
FIG. 6 is a graph showing a comparison of cell yield from the same donor tissue digested using an example of the method of the invention and a process benchmark.

Isolation of monodispersed cells from different donors using different agitation methods: The monodispersed cell yield from donor tissues digested using either jet mixing or a benchmark process (orbital shaker) is compared. 50-100 g of lipoaspirate from donors A, B, and D were washed seven times with an equal volume of pre-warmed (37° C.) Lactated Ringer's to remove excess blood/saline. Buoyant adipose tissue was digested at 37° C. with concentrations of 0.5 U/mL Liberase and 50 U/mL Thermolysin, for donor A and B, and 0.3 U/mL Liberase and 15 U/mL Thermolysin for donor D in 50-100 mL Lactated Ringer's, as shown in FIG. 6, with two different types of mixing, namely pump-assisted jet mixing (flow rate 450 mL/min) for 15 minutes and orbital mixing (~95 rpm) for 20 minutes on a platform shaker. After digestion, aqueous fractions containing monodispersed cells were pooled and filtered through 100-micron cell strainers to remove debris.

Measurement of total cell yield per gram adipose following jet mixing or process benchmark digestion: Total nucleated cell counts were determined using a Nucleocounter for tissues digested by jet mixing or process benchmark. Measurements were conducted in duplicate and multiplied by a dilution factor to back-calculate cells/g of original tissue.

The result of the experiment demonstrated enhanced cell yield, wherein the cell yield improved significantly with jet mixing. In FIG. 6, at an equivalent concentration of digestive enzymes, a repeatable increase in cell yield with jet-mixing over the non-jet mixing (the process benchmark) procedure is observed among same-donor tissue and the increase appears consistent for different donors. Increased cell yield for donors A and B in case of jet mixing over process benchmark are shown in Table 1.

TABLE 1

Comparison of cell yield from same-donor tissues using jet mixing or process benchmark

| Donor | Mode of processing | Enzyme used (Liberase, Thermolysin) | Yield/g |
|---|---|---|---|
| A | Benchmark | 0.5 U/mL Lib, 50 U/mL Ther | 656640 |
|   | Jet mixing | 0.5 U/mL Lib, 50 U/mL Ther | 1494318 |
| B | Benchmark | 0.5 U/mL Lib, 50 U/mL Ther | 838764 |
|   | Jet mixing | 0.5 U/mL Lib, 50 U/mL Ther | 1642282 |

Example 2

Cell Viability with Reduced Enzyme Concentration

Isolation of monodispersed cells from a donor using different agitation methods: The monodispersed cell yield and viability from a donor tissue digested using either jet mixing or a benchmark process (orbital shaker) is compared. 50-100 g of lipoaspirate from donor D was washed seven times with an equal volume of pre-warmed (37° C.) Lactated Ringer's to remove excess blood/saline. Buoyant adipose tissue was digested at 37° C. with concentrations of 0.3 U/mL Liberase and 15 U/mL Thermolysin for donor D in 50-100 mL Lactated Ringer's, as shown in FIG. 6, with two different types of mixing, namely pump-assisted jet mixing (flow rate 450 mL/min for 15 minutes) and orbital mixing (~95 rpm for 20 minutes) on a platform shaker. After digestion, aqueous fractions containing monodispersed cells were pooled and filtered through 100-micron cell strainers to remove debris.

Cell yield and viability: Total nucleated cell counts and dead cells (per mL) were determined using a Nucleocounter for same-donor tissue digested by jet mixing or process benchmark. Dead cell counts were subtracted from total nucleated cells counts to calculate viable nucleated cells/mL in addition to percent viability. The strength of the jet mixing-mediated digestion with much less enzyme usage (e.g. 0.3 U/mL Liberase, 15 U/mL Thermolysin) increased post-digest cell yield without significant reduction of overall cell viability as shown in Table 2. The invention is not limited to the specific amount of enzymes, yield, or viability. The viability may increase without the jet mixing depending upon the enzyme used and in what amount. The experiment also demonstrated the ability to make equivalent yield at reduced amount of enzyme and enables similar viability. Under enzyme concentrations classically used for digestion, jet mixing yields a greater pool of cells, including regenerative cells, from adipose tissue. In addition, the experiment demonstrated that jet mixing enables similar high yields and high viability with greatly reduced enzyme concentration, as shown for donor D in Table 2.

TABLE 2

Comparison of Cell Yield and Viability at Reduced Enzyme Concentration

| Donor | Mode of processing | Enzyme used (Liberase, Thermolysin) | Yield/g | Viability (%) |
|---|---|---|---|---|
| D | Benchmark | 0.3 U/mL Lib, 15 U/mL Ther | 381189 | 70.8 |
|   | Jet mixing | 0.3 U/mL Lib, 15 U/mL Ther | 1303432 | 67.3 |

Example 3

Jet Mixing Allows Faster Digestion

Monodispersed cells were isolated from one or more donors using different agitation methods, such as process benchmark or jet mixing. The jet-mixing allows faster digestion of adipose tissue, which is conveyed in Table 3. In the experiment, same-donor tissue (say, donor A) was digested for 20 minutes with the benchmark, while the jet-mediated digestion was performed for only 15 minutes. In the same experiment, while the tissues were isolated from different donors, such as A. B, or D and then digested for 20 minutes in case of the benchmark process and for only 15 minutes in case of the jet-mediated digestion process, the cell yield per gram of cells is repeatedly increased for jet mixing process. Table 3 demonstrates that superior cell yield per gram of adipose tissue is achieved for less digestion time using jet-mixing compared to benchmark, even if using less enzyme concentration (for donor D).

TABLE 3

Cell yield for different digestion time

| Donor | Mode of processing | Enzyme used (Liberase, Thermolysin) | Digestion time (minutes) | Yield/g |
|---|---|---|---|---|
| A | Benchmark | 0.5 U/mL Lib, 50 U/mL Ther | 20 | 656640 |
|   | Jet mixing | 0.5 U/mL Lib, 50 U/mL Ther | 15 | 1494318 |
| B | Benchmark | 0.5 U/mL Lib, 50 U/mL Ther | 20 | 838764 |
|   | Jet mixing | 0.5 U/mL Lib, 50 U/mL Ther | 15 | 1642282 |
| D | Benchmark | 0.3 U/mL Lib, 15 U/mL Ther | 20 | 381189 |
|   | Jet mixing | 0.3 U/mL Lib, 15 U/mL Ther | 15 | 1303432 |

Example 4

Characteristics of Cells Isolated from Adipose Tissue by Jet Mediated Digestion Procedure Preparation of monodispersed viable cells from different donors: Monodispersed cells from donors #1 and #2 were prepared by jet-mediated digestion using Liberase collagenase and Thermolysin neutral protease. Equal volumes of lipoaspirate and pre-warmed (37° C.) Lactated Ringer's were mixed in a mixing vessel (for example, separatory funnel chamber) using the jet mixer and allowed to settle for at least 30 seconds. Excess blood/saline was drained from the buoyant adipose tissue layer, and the tissue was washed about 6 times with Lactated Ringer's using pump-assisted jet mixing. A solution containing Liberase in a range of 0.15-0.3 U/mL and Thermolysin in a range of 7.5-15 U/mL in 100 mL Lactated Ringer's was poured into the mixing vessel (separatory funnel chamber) comprising the jet mixer and agitated with adipose tissue for 25 minutes at 37° C. using jet mixer. Non-buoyant aqueous fractions containing monodispersed cells were collected after digestion and filtered through 100-micron cell strainers to remove debris. Total nucleated cell yield and percent viability for Donors #1 and #2 were ~$6 \times 10^5$ cells/mL (66% viability) and ~$1 \times 10^6$ cells/mL (51% viability), respectively.

Processing of monodispersed cells for FACS analysis: Monodispersed cells were pelleted at 800×g for 10 minutes at room temperature and re-suspended in 160 mM $NH_4Cl$ to lyse red blood cells. After 10-minute incubation at room temperature, nucleated cells were pelleted by centrifugation at 500×g, for 10 minutes, at room temperature and re-suspended in 10% normal mouse serum in PBS. After blocking for 30 minutes at 4° C., cells were pelleted at 500×g, for 5 minutes, at 4° C. and re-suspended in 1% normal mouse serum in PBS. 100 μL aliquots containing $1 \times 10^6$ cells were pipetted into microcentrifuge tubes containing the following dye-conjugated antibodies in specific combinations: CD31-FITC, CD34-PE, CD45-PE-Cy5, CD9O-PE-Cy5, CD29-PE-Cy5, CD63-FITC, CD44-FITC and CD59-FITC. Additional control samples were incubated without antibody or in the presence of mouse IgG1-FITC or IgG2a/2b-FITC to assess non-specific background. Cells were incubated for 30 minutes at 4° C. protected from light, and fixed for 15 minutes at room temperature with 1-Step Fix/Lyse Solution for labeling the cells.

Figure 7:
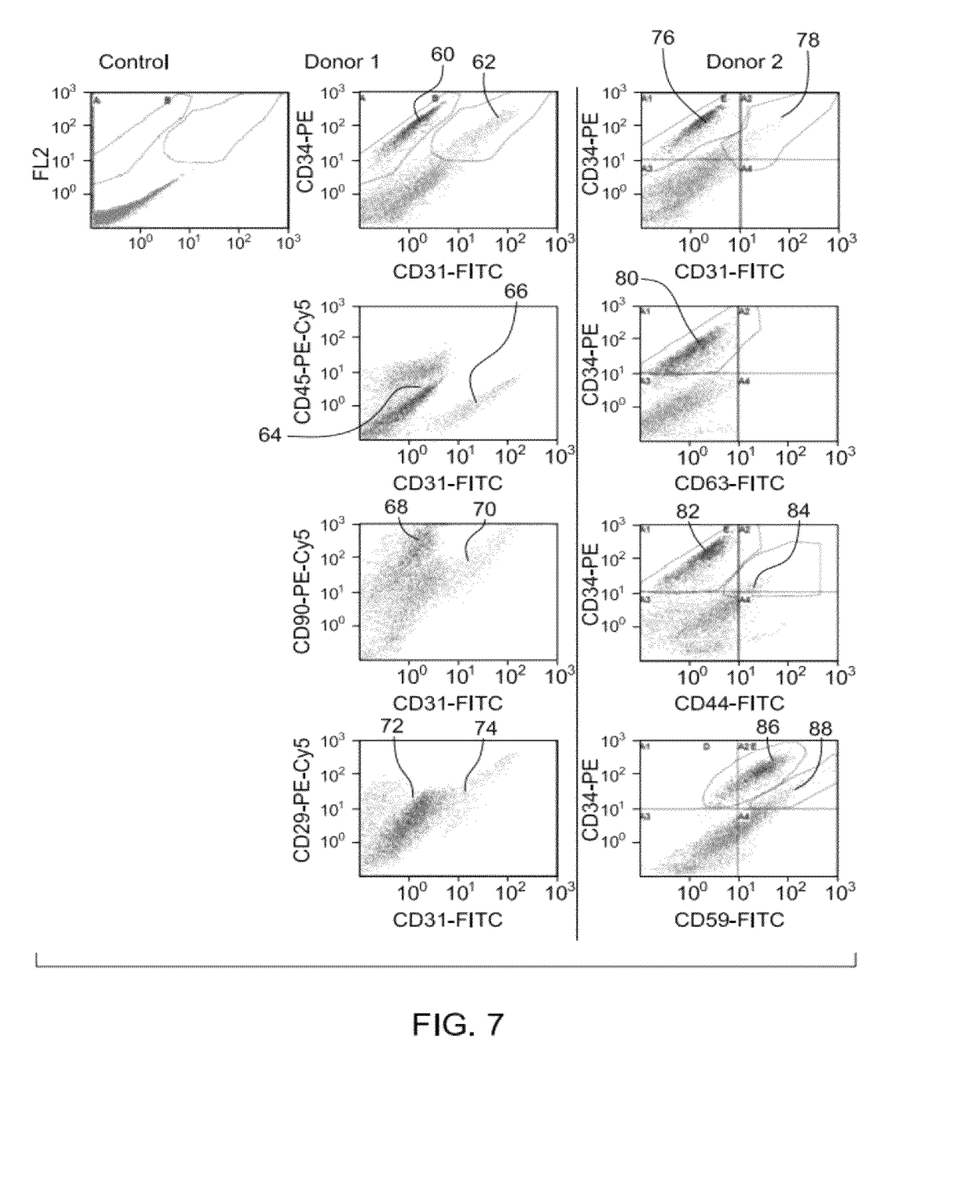
FIG. 7 is a series of graphs from fluorescence activated cell sorting (FACS) analysis showing various markers of adipose derived stem cells (ADSC) and endothelial progenitor cells isolated from two different donor tissues using an example of a method and system of the invention.

Characterization by Fluorescence Activated Cell Sorting (FACS) analysis: Labeled cells were washed twice with flow buffer (PBS, 0.5% BSA, 0.1% azide) and detected by multi-color flow cytometry using a Cytomics FC-500. FITC-labeled, PE-labeled, and PE-Cy5 labeled antibodies were detected simultaneously using green, yellow, and red fluorescent channels, respectively. All data were acquired without gates, and specific cell populations were color-coded and quantified using MXP Software following acquisition as shown in FIG. 7. Gates labeled in 60, 64, 68, and 72 for donor 1, and 76, 80, 82, and 86 for donor 2 (red in original colored version) in the FIG. 7 represent adipose derived stem cells (ADSC)-like cells having markers CD31− CD34+ CD45− CD90+ CD29$^{lo}$ CD63− CD44− CD59$^{lo}$, whereas gates labeled in 62, 66, 70 and 74 for donor 1, and 78, 84 and 88 for donor 2 (green in original colored version) appear to be endothelial progenitor cells having markers CD31+ CD34+ CD45− CD90+ CD29$^{hi}$ CD63− CD44$^{lo}$ CD59$^{hi}$. Cells from both donors show similar staining patterns using jet-mediated digestion. Therefore, the population of regenerative cells isolated from adipose tissue by jet-mediated digestion of the invention comprises ADSC-like cells, and endothelial progenitor cells.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A mixing vessel for processing an adipose tissue to collect adipose derived regenerative cells, comprising:
   at least one inlet port for receiving adipose tissue, a buffer and an enzyme solution;
   a centrally located cylinder comprising one or more nozzles configured to generate a high velocity fluid stream, wherein the nozzles are in an upward direction to generate an upward fluid stream and a jet mixing into the vessel to digest adipose tissue and form a digested buoyant fat layer and a non-buoyant aqueous layer comprising adipose derived regenerative cells;
   at least one outlet port comprising a filter unit, wherein the filter unit allows to pass the non-buoyant aqueous layer comprising adipose derived regenerative cells,
   wherein the cylinder is operably connected to the inlet port and the outlet port.

2. The mixing vessel of claim 1, wherein the outlet port is operably connected to a pump.

3. A system for isolating regenerative cells from an adipose tissue, comprising:
   a mixing vessel comprising:
   at least one inlet port for receiving adipose tissue, a buffer and an enzyme solution;
   a centrally located cylinder comprising one or more nozzles configured to generate a high velocity fluid stream, wherein the nozzles are in an upward direction to generate an upward fluid stream and a jet mixing into the vessel to digest adipose tissue and form a digested buoyant fat layer and a non-buoyant aqueous layer comprising adipose derived regenerative cells;
   at least one outlet port comprising a filter unit, wherein the filter unit allows to pass the non-buoyant aqueous layer comprising adipose derived regenerative cells,
   wherein the cylinder is operably linked to the inlet port and the outlet port;
   one or more containers and
   one or more fluid circuit tubing is operably connected to the mixing vessel, and to the containers.

4. The system of claim 3, further comprising a direct current (DC) servo motor.

5. The system of claim 3, further comprising one or more multi-port valves.

6. The system of claim 3, wherein the fluid circuit tubing further comprises a filter unit.

7. The system of claim 3, wherein the centrally located cylinder of the mixing vessel comprises at least four nozzles.

8. The system of claim 3, wherein the fluid circuit tubing is operably connected to one or more pumps.

9. The system of claim 3, further comprising a sensor configured to measure mass of the mixing vessel and the containers.

10. The system of claim 3 is enclosed in a chamber, wherein the chamber comprises a temperature controller.

11. The system of claim 10, wherein the chamber further comprises a fan heater.

* * * * *